United States Patent
Masters et al.

(10) Patent No.: US 6,290,935 B1
(45) Date of Patent: Sep. 18, 2001

(54) DUAL COMPONENT ORAL COMPOSITION HAVING ACCELERATED TOOTH WHITENING EFFECT

(75) Inventors: James G. Masters, Ringoes; Robert J. Gambogi, Belle Mead; Mike Wong, Plainsboro; Diego A. Hoic, Highland Park; Vincent O. Drago, Sayerville, all of NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 09/621,363

(22) Filed: Jul. 21, 2000

(51) Int. Cl.⁷ ............................... A61K 7/16; A61K 7/20
(52) U.S. Cl. .................................. 424/53; 424/49
(58) Field of Search .................................. 424/53

(56) References Cited

U.S. PATENT DOCUMENTS

| | | | |
|---|---|---|---|
| 4,069,310 | * | 1/1978 | Harrison . |
| 4,081,526 | * | 3/1978 | Asakawa et al. . |
| 4,537,765 | * | 8/1985 | Gaffar et al. . |
| 4,828,723 | * | 5/1989 | Cao et al. . |
| 4,846,992 | * | 7/1989 | Fonsny . |
| 4,931,195 | * | 6/1990 | Cao et al. . |
| 5,004,556 | * | 4/1991 | Julemont et al. . |
| 5,032,178 | * | 7/1991 | Cornell . |
| 5,648,064 | * | 7/1997 | Gaffar et al. . |
| 5,766,574 | * | 6/1998 | Beck et al. . |
| 5,814,304 | * | 9/1998 | Wong et al. . |
| 5,815,514 | * | 12/1998 | Wong et al. . |
| 5,976,508 | * | 11/1999 | Wabi et al. . |
| 6,106,293 | * | 8/2000 | Wiesel . |
| 6,106,812 | * | 8/2000 | Prencipe et al. . |
| 6,110,446 | * | 8/2000 | Prencipe et al. . |

FOREIGN PATENT DOCUMENTS

| | | | |
|---|---|---|---|
| 332551 | * | 9/1989 | (EP) . |
| 2 0000 59461 | * | 10/2000 | (WO) . |

* cited by examiner

*Primary Examiner*—Shep K. Rose
(74) *Attorney, Agent, or Firm*—Paul Shapiro

(57) ABSTRACT

Two component whitening dentifrice composition which exhibits rapid whitening of stained or discolored teeth, which composition comprises a first dentifrice component containing a peroxide compound and the second component containing Fe ion implanted silicate clay, the first and second dentifrice components being maintained separate from each other until dispensed for application to teeth requiring the removal of stain and discoloration.

12 Claims, No Drawings

DUAL COMPONENT ORAL COMPOSITION HAVING ACCELERATED TOOTH WHITENING EFFECT

BACKGROUND OF THE INVENTION

1. Field of the Invention

This invention relates generally to an oral composition which when applied onto the surface of teeth acts to whiten teeth and more particularly a dual component peroxide containing composition for whitening teeth that is more effective than existing products available to the consumer.

2. The Prior Art

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Stains associated with teeth are caused by the presence of chomophores (colored agents). These chromophores arise from two chemical sources—organic compounds, such as carotene, inorganic transition metal ions, such as iron and tin, and combinations, such as blood having both iron and the colored porphyrin ligand. These stains can reside as extrinsic stain on the surface of the teeth and/or as intrinsic stain within the teeth Extrinsic stain can be removed by abrasion and/or bleaching. However, intrinsic stain, is bonded within the structure of the tooth cannot be reduced by brushing or any abrasive process, but can only be reduced only with a penetrating bleaching agent.

Intrinsic stain can occur from several processes. Before tooth eruption, ingestion of excess fluoride leads to fluorosis stain. Use of tetracycline during tooth development can produce stain due to the antibiotic binding to the hydroxyapatite crystals a mineral component of teeth. Developmental disorders such as arnelogenesis imperfects and dentinogenesis imperfects can cause pre-eruptive tooth stain. Hematologic diseases such as erythroblastosis fetalis and sickle-cell anemia can lead to blood in the dentin tubules and intrinsic stain.

Teeth can acquire intrinsic stain after eruption. Trauma to the teeth can cause bleeding within the pulpal cavity and penetration of blood into the dentin tubules. Dental procedures such as amalgam restorations can release metals into the dentin. Incomplete obturation of pulp chamber during endodontic treatment can also lead to intrinsic tooth stain.

Extrinsic stain results from binding of chromophores to the tooth surface by attractive forces such as electrostatic, van der Waals and hydrogen bonding. Many foods and beverages contain staining chromophores which can deposit directly to the teeth. Tea, coffee and wine, for example, contain darkly colored tannins that produce stain. Likewise, tobacco products can cause extrinsic stain. Calculus build up on the teeth can be perceived as extrinsic stain. Although calculus is naturally white, it can act as a reservoir to bind and trap chromophores from food and beverages. Similarly, the normally colorless plaque and pellicle can act as sites for binding staining chromophores to the teeth.

There are available in the marketplace oral compositions for home use which contain 1–3% by weight concentrations of a peroxide compound such as hydrogen peroxide and when applied on the teeth effect whitening of stains. However, these compositions are considered to have a slow bleaching effect.

Illustrative of oral compositions containing peroxygen compounds for whitening teeth include U.S. Pat. Nos. 5,648,064, 5,279,816, 4,988,450; 4,980,152, 4,839,156, 4,405,599, 3,988433 and 3,657,417.

U.S. Pat. No. 5,648,064 discloses a two component whitening dentifrice composition which comprises a first component containing a peroxide compound such as hydrogen peroxide and a second dentifrice component containing a manganese coordination complex compound such as manganese gluconate, which activates the peroxide compound and accelerates the release of active oxygen to accelerate whitening action when intermixed with the peroxide compound, the first and second components being maintained separate from the other until dispensed for application to teeth.

U.S. Pat. No. 5,279,816 discloses an oral composition for whitening teeth containing peracetic acid dissolved or suspended in a vehicle. U.S. Pat. No. 5,302,374 discloses generating peracetic acid within a dentifrice vehicle by combining water, acetylsalicylic acid and a water soluble alkali metal percarbonate.

U.S. Pat. Nos. 4,988,450 and 3,657,417 disclose formulating oxygen liberating compositions for the whitening of teeth utilizing anhydrous pastes or gels.

U.S. Pat. No. 4,980,152 discloses an aqueous oral gel composition comprising about 0.5 to about 10% by weight urea peroxide and 0.01 to 2% by weight of a fluoride providing compound.

U.S. Pat. No. 4,839,156 discloses a water containing a hydrogen peroxide-Pluronic thickened oral gel composition.

In those applications where oral compositions are designed for home use whitening of teeth, it is essential that the peroxide generating components react quickly since the user will normally wish to limit the time in which the whitening composition is in contact with the teeth. To accomplish this, applicant has recognized the desirability of accelerating the breakdown of peroxide compounds and the release of active oxygen within the oral cavity to effect a more rapid whitening of the teeth.

The art continues to seek oral compositions which accomplish accelerated whitening of teeth.

SUMMARY OF THE INVENTION

In accordance with the present invention there is provided a peroxide containing oral composition effecting accelerated whitening of teeth wherein there is provided a two component composition of separate unmixed phases comprised of (a) a first component containing a water soluble peroxide compound contained in an orally acceptable vehicle and (b) a second component containing a Fe ion implanted synthetic silicate clay matrix in an orally acceptable vehicle in an amount effective to activate the peroxide compound and accelerate the release of active oxygen when mixed therewith, the two phases being combined shortly before application to the teeth wherein the Fe ion implanted clay interacts with the peroxide constituent to accelerate the breakdown and rapid release of active oxygen from the peroxide compound such rapid release being effective to enhance tooth whitening when allowed to remain on the teeth for a limited time.

DETAILED DESCRIPTION OF THE INVENTION

Peroxide compounds useful in the oral compositions of the invention include hydrogen peroxide, peroxydiphosphate, urea peroxide, metal peroxides such as calcium peroxide, sodium peroxide, stronthium peroxide, magnesium peroxide, and the salts of perborate, persilicate, perphosphate and percarbonate such as sodium perborate, potassium persilicate and sodium percarbonate. The most suitable peroxide compound for this invention is hydrogen peroxide.

The amount of peroxide compound incorporated in the first component of the two component oral composition of the present invention will vary dependent upon its intended use. For use by trained professionals in office treatments, the concentration of peroxide compound incorporated in the oral composition can vary from about 5 to about 30% by weight. For home use, such high concentrations of peroxide compounds cannot be used safely by the typical consumer and therefore the useful range of peroxide compound when the oral composition is a paste, gel or rinse is between about 0.1 to about 3.0% by weight. The preferred range is between about 0.5 to about 2.0% by weight.

Implantable synthetic silicate clay matrices useful in the practice of the invention are known to the art (U.S. Pat. No. 4,049,788) and include synthetic hectorite, a synthetic colloidal magnesium alkali metal silicate complex clay commercially available under the trade designation, Laponite, from Laporte Industries Limited. Laponites are synthetic hectorite clays composed of magnesium, lithium, silica, oxygen, hydrogen, and sodium. One form of Laponite, Laponite D, analysis shows, approximately by weight, 58.00% $SiO_2$, 25.40% MgO, 3.05% $Na_2O$, 0.98% $Li_2O$ and some water and trace metals. Its true specific gravity is 2.53 and it has an apparent bulk density (g./ml. At 8% moisture) of 1.0 and is known to the dentifrice art as a useful thickener for dentifrice compositions as for example U.S. Pat. No. 4,069.3 10.

Like other clays, Laponites are composed in the dry state of platetlets arranged in stacks. Each platelet has a double layer of tetrahedral silica bonded to oxygen atoms. Between the two silica layers there is a sheet of cations composed of magnesium and lithium in a 5.3 to 0.7 ratio. These cations coordinate the inner row of silica bound oxygens and OH groups. During the preparation and synthesis of synthetic clay matrices, Fe atoms in the 2+ or 3+ oxidation state may be substituted for alkali and/or alkaline metals within the inner octahedral layer of the clay. The partial substitution of Mg ion with Fe results in an implanted hectorite clay which functions, when incorporated in the second component of a dual component dentifrice of the present invention as a peroxide activator when combined with a first dentifrice component containing a peroxide compound such as hydrogen peroxide, urea peroxide or calcium peroxide.

Synthetic silicate clay implanted with about 0.01 to about 10% by weight Fe ion and preferably about 0.5 to about 5% by weight has been determined to provide unexpected enhanced activation of peroxide compounds when combined therewith.

The amount of Fe ion implanted clay incorporated in the second component of the two phase whitening dentifrice composition of the present invention will vary dependent upon the amount of peroxide compound incorporated in the first component. When the whitening oral composition of the present invention is to be used by trained professionals and the first component contains relatively high concentrations of a peroxide compound, e.g. 5 to 35% by weight, the amount of Fe ion implanted synthetic silicate clay activator compound incorporated in the second component will range between 0.1 to 3% by weight and preferably between 0.25 to 1.75% by weight. For home use oral compositions in which the concentration range of peroxide compound in the first oral composition component is between about 0.1 to about 3.0% by weight, concentrations, e.g., between about 0.05 to about 7.0% by weight of the Fe ion implanted synthetic silicate clay activator is included in the second component and preferably about 0.05 to about 3.0% by weight of the activator is used.

In the preparation of both dentifrice components of the present invention, the respective peroxide and Fe ion implanted synthetic silicate clay activator ingredients are incorporated within a pharmaceutically-acceptable vehicle suitable for use in the oral cavity, which contains water, humectant, surfactant and a polishing agent or abrasive.

The humectant is generally a mixture of humectants, such as glycerol, sorbitol and polyethylene glycol of a molecular weight in the range of 200–1000, but other mixtures of humectants and single humectants may also be employed. The humectant content within each of the two components is in the range about of 10% to about 30% by weight and preferably about 10 to about 20% by weight. The water content which is from about 20% to about 55%, and preferably from about 25 to 50% by weight.

Polishing agents or abrasives which may be present in both components of the dentifrice include sodium metaphosphate, potassium metaphosphate, tricalcium phosphate, dihydrated dicalcium phosphate calcined alumina and siliceous materials or combinations thereof. Preferred polishing agents include dicalcium phosphate and siliceous materials, such as silica and more preferably a precipitated amorphous hydrated silica, such as Zeodent 115, marketed by J. M. Huber Chemicals Division, Havre de Grace, Md. 21078, or Sylodent 783 Sylodent XWA 300 available from Grace Davison, Baltimore, Md. 21203.

Organic or inorganic thickeners may be included in the dentifrice of the present invention. Organic thickeners such as natural and synthetic gums and colloids may also be incorporated in the present invention. Examples of such organic thickeners include carrageenan (Irish moss), xanthan gum and sodium carboxymethyl cellulose, starch, polyvinylpyrrolidone, hydroxyethylpropyl cellulose, hydroxybutyl methyl cellulose, hydroxypropylmethyl cellulose, and hydroxyethyl cellulose. Inorganic thickeners such as Laponite D are preferred, as well as amorphous silica compounds which function as thickening agents including, colloidal silica compounds available under tradenames such as Cab-o-sil fumed silica manufactured by Cabot Corporation and distributed by Lenape Chemical, Bound Brook, N.J., Zeodent 165 from J. M. Huber Chemicals Division, Havre de Grace, Md. 21078 and Sylox 15 from Grace Davison, Baltimore, Md. 21203. Either inorganic or organic thickening agents, or combinations thereof, may be present in both components of the dentifrice in proportions of about 0.1 to about 10% by weight, preferably about 5 to about 8% by weight in each of the two components of the dentifrice.

Surface active agents or surfactants may be incorporated in both components of the present invention as an ingredient to aid in the thorough dispersion of the dentifrice throughout the oral cavity when applied thereto, as well as, to improve cosmetic acceptability and the foaming properties. The surface active agents which can be included within the vehicle of both components of the present invention include anionic, nonionic or amphoteric compounds, anionic compounds being preferred.

Suitable examples of anionic surfactants are higher alkyl sulfates such as potassium or sodium lauryl sulfate which is preferred, higher fatty acid monoglyceride monosulfates, such as the salt of the monosulfated monoglyceride of hydrogenated coconut oil fatty acids, alkyl aryl sulfonates such as sodium dodecyl benzene sulfonate, higher fatty sulfoacetates, higher fatty acid esters of 1,2 dihydroxy propane sulfonate.

Examples of water soluble nonionic surface active agents are condensation products of ethylene oxide with various hydrogen-containing compounds that are reactive therewith and have long hydrophobic chains (e.g., aliphatic chains of about 12 of 20 carbon atoms), which condensation products contain hydrophilic polyoxyethylene moieties, such as condensation products of poly (ethylene oxide) with fatty acids, fatty alcohols, fatty amides and other fatty moieties, and with propylene oxide and polypropylene oxides, e.g., Pluronic® materials such as Pluronic F127.

The surface active agent can be present in one or both components of the instant inventive compositions of the present invention at a concentration of about 0.5 to about 5.0% by weight, preferably about 1 to about 2% by weight of the particular component.

Linear molecularly dehydrated polyphosphate salts can be employed as anticalculus agents. They are well known, being generally employed in the form of their wholly or partially neutralized water soluble alkali metal (e.g. potassium or sodium or ammonium salts, and any mixtures thereof. Representative examples include sodium tripolyphosphate, monosodium triacid-, disodium diacid-, trisodium monoacid-, and tetrasodium-pyrophosphates, the corresponding potassium salts and the like. In the present invention, they can be employed in the oral compositions in approximate weight amounts of about 0.1 to about 3%, typically about 1 to about 2.5%, more typically about 1.5 to about 2%, especially about 2%. Preferred anticalculus agents are tetrasodium pyrophosphates (TSPP), sodium tripolyphosphate (STPP), and mixtures thereof.

Fluoride ions may also be included in the dentifrice compositions of the present invention to provide an anticaries effect. Among these materials are inorganic fluoride salts, such as soluble alkali metal fluoride salts, for example, sodium fluoride, potassium fluoride, sodium monofluorophosphate and sodium hexafluorosilicate. Alkali metal fluorides, such as sodium fluoride, sodium monofluorophosphate, sodium hexafluorosilicate and mixtures thereof, are preferred.

The amount of fluorine-providing salt is generally present in the oral composition at a concentration of about 0.0005 to about 3.0% by weight. Any suitable minimum amount of such salt may be used, but it is preferable to employ sufficient fluoride salt to release about 300 to 2,000 ppm, more preferably about 800 to about 1,500 ppm, of fluoride ion.

A striped dentifrice product may be obtained using the multicomponent dentifrice of the present invention, wherein colorants of contrasting colors are incorporated in each of the dentifrice components to be dispensed; the colorants being pharmacologically and physiologically non-toxic when used in the suggested amounts. Colorants used in the practice of the present invention include both pigments and dyes.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The concentration of the dye in the dentifrice composition in an amount from about 0.0005 percent to about 2 percent by weight of the respective component.

Other agents which may be present in the compositions of the present invention include about 0.05 to about 5% by weight, preferably about 0.1 to about 3% by weight of a natural or synthetic anionic polycarboxylates having a molecular weight of about 1,000 to about 5,000,000, preferably about 30,000 to about 500,000. Synthetic anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl either/maleic anhydride having a molecular weight (M.W.) of about 30,000 to about 1,000,000, most preferably about 30,000 to about 500,000. These copolymers are available, for example, under the trade designation Gantrez AN 139 (M.W. 500,000), AN 119 (M.W. 250,000); and preferably Gantrez S-97 Pharmaceutical Grade (M.W. 70,000), of GAF Corporation.

Other anionic polycarboxylates useful in the practice of the present invention include the 1:1 copolymers of maleic anhydride with ethyl acrylate, hydroxyethyl methacrylate, N-vinyl -2-pyrollidone, or ethylene, the latter being available, for example, as Monsanto EMA No: 1103, M.W. 10,000 and Grade 61, and 1:1 copolymers of acrylic acid with methyl or hydroxyethyl methacrylate, methyl or ethyl acrylate, isobutyl methacrylate, isobutyl vinyl ether or N-vinyl-2-pyrrolidone.

Additional operative useful polycarboxylate compounds include copolymers of maleic anhydride with styrene, isobutylene or ethyl vinyl either, polyacrylic, polycationic and polymaleic acids, and sulfonacrylic oligomers of M.W. as low as 1,000 available under the trade designation Uniroyal ND-2.

Also useful in the practice of the present invention are the so-called carboxyvinyl polymers, commercially available, for example, under the trade designation Carbopol 934, 940 and 941 from B.F. Goodrich, these polymers consisting of a colloidally water-soluble polymer of polyacrylic acid crosslinked with from about 0.75% to about 2.0% of polyallyl sucrose or polyallyl pentaerythritol as a cross linking agent, often with molecular weights in the range of 4–5 million.

In the preparation of the dual component whitening dentifrice composition of the present invention, the first component contains the peroxide whitening agent and the second component contains the Fe ion implanted synthetic silicate clay activator. The components when combined, are combined in approximately equal weight proportions, so that only about one-half of the concentration of any particular ingredient within either component will be present when the components are combined and applied to the teeth, as by brushing. Both components are formulated with similar vehicle ingredients, with the significant exception being the presence of the peroxide in the first component and the and the Fe ion implanted clay in the second component. This similarity of vehicle ingredients is to provide similar physical characteristics to promote similar rheology so that the two components are delivered simultaneously in the desired equal measure by extrusion from a dual compartmented tube or pump device.

To prepare the first peroxide component of the present invention, the humectants, e.g., glycerin, polyethylene glycol, sweetener and water are dispersed in a conventional mixer until the mixture becomes a homogeneous gel phase. Into this gel phase is added an anticaries agent such as sodium fluoride. Also added are any tartar control ingredients such as tetrasodium pyrophosphate, and any inorganic thickening agents. Into this phase is added polycarboxylate additives such as Carbopol dispersed in polyethylene glycol, and the ingredients are mixed under vacuum until a homogeneous phase is obtained. Thereafter peroxide, phosphoric acid flavor, any surfactant, as well as any dye or pigment are added. The resulting ingredients are mixed at high speed under vacuum, and the resultant product is a homogeneous, semi-solid, extrudable dentifrice.

To prepare the second Fe ion implanted synthetic silicate clay activator containing component, of the present invention, the humectants e.g. propylene glycol, glycerin, polyethylene glycol ingredients, sweetener and water are dispersed in a conventional mixer until the mixture becomes a homogeneous gel phase. Into the gel phase are added a pigment such as $TiO_2$ and any tartar control agents such as tetrasodium pyrophosphate or sodium tripolyphosphate or both and fluoride anti-caries agents such as sodium monofluorophosphate. These ingredients are mixed until a homogeneous phase is obtained. Thereafter the Fe implanted synthetic silicate activator thickener, polishing agent, flavor and surfactant ingredients are added and the ingredients mixed at high speed under vacuum of about 20–100 mm Hg. The resultant product is a homogeneous, semi-solid, extrudable paste product.

The two component dentifrice composition of the present invention may be packaged in a suitable dispensing container in which the components are maintained physically separated and from which the separated components may be dispensed synchronously as a ribbon for application to a toothbrush. Such containers are known in the art. An example of such a container is a two compartment dispensing container having collapsible sidewalls, as disclosed in U.S. Pat. Nos. 4,487,757 and 4,687,663 wherein the container body is formed from a collapsible plastic web and is provided with a partition within the container body defining separate compartments in which the physically separated components are stored and from which they are dispensed through a suitable dispensing outlet.

The following examples are further illustrative of the present invention, but it is understood that the invention is not limited thereto. All amounts and proportions referred to herein and the appended claims are by weight.

EXAMPLE I

Laponite D was implanted with Fe ion. Analysis of the Fe ion implanted Laponite D showed that Fe ion was substituted for Mg ion as compared to the standard Laponite D silicate. Electron Spectroscopy for Chemical Analysis (ESCA) data was used to calculate the empirical formula of the Fe implanted Laponite D which is shown below:

Laponite Fe—$Na_{0.9}+[(Si_8Mg_4Li_{0.3}Fe_{0.44})O_{20}(OH)_4]_{0.7}$ whereby the Fe content was determined to be approximately 3% by weight of the clay product.

The theoretical formula of Laponite D is $Na_{0.7}+[(Si_8Mg_4Li_{0.3})O_{20}(OH)_4]_{0.7}$ and the formula as determined from ESCA measurements is $Na_{0.6}+[(Si_8Mg_{4.5}Li_{0.3})O_{20}(OH)_4]_{0.7}$.

The Fe ion implanted Laponite D was added to a toothpaste component at a level of 1% by weight resulting in an iron concentration in the component of 0.03% by weight.

A dual component dentifrice designated Composition "X" containing 1% Fe ion implanted Laponite D was prepared having two separate components designated Components A and B containing the ingredients listed in Table I below.

For purposes of comparison, a comparative dentifrice composition designated Composition "Y" was prepared having two dentifrice components C and D containing ingredients similar to that of Composition X except that unmodified Laponite D was used instead of Fe implanted Laponite D and manganese gluconate a known (U.S. Pat. No. 5,648,064) peroxide accelerator used in peroxide dentifrices was substituted for Fe ion Laponite D. For purposes of further comparison, a third composition designated Composition Z having components E and F was prepared in which unmodified Laponite substituted for the Fe implanted Laponite D. The ingredients of these compositions are also listed in Table I below.

TABLE I

| Ingredients | Composition | | | | | |
|---|---|---|---|---|---|---|
| | X | | Y | | Z | |
| | Components | | | | | |
| | A (Wt. %) | B (Wt. %) | C (Wt. %) | D (Wt. %) | E (Wt. %) | F (Wt. %) |
| Glycerine (95%) | 40.00 | 12.0 | 40.0 | 12.0 | 10.0 | 13.0 |
| Sorbitol | — | 27.6 | — | 27.6 | 8.0 | — |
| PEG 600 | 10.0 | — | 10.0 | — | — | — |
| Sodium lauryl sulfate | — | 2.2 | — | 2.2 | — | 3.0 |
| Betaine (30% soln.) | — | — | — | — | — | 2.0 |
| Pluronic F-127 | — | — | — | — | 1.50 | — |
| Xanthan gum | 0.40 | — | 0.4 | — | 1.0 | 1.1 |
| Carrageenan | — | 0.35 | — | 0.35 | — | — |
| Carboxymethyl cellulose | — | 0.80 | — | 0.80 | — | — |
| Carbopol 974 | 2.00 | — | 2.0 | — | — | — |
| Gantrez | — | 7.69 | — | 7.69 | — | — |
| STPP | — | 7.0 | — | 7.0 | — | — |
| Laponite D | 0.1 | — | 0.10 | 0.75 | 1.0 | — |
| Fe Laponite | — | 1.0 | — | — | — | — |
| Mn gluconate | — | — | — | 0.05 | — | — |
| Flavor | 0.30 | 1.9 | 0.30 | 1.90 | 1.15 | 1.15 |
| Sodium fluoride | 0.243 | 0.243 | 0.243 | 0.243 | — | 0.486 |

TABLE I-continued

| | Composition | | | | | |
|---|---|---|---|---|---|---|
| | X | | Y | | Z | |
| | | | Components | | | |
| Ingredients | A (Wt. %) | B (Wt. %) | C (Wt. %) | D (Wt. %) | E (Wt. %) | F (Wt. %) |
| Sodium hexafluorosilicate | — | — | — | — | 0.239 | 0.30 |
| Titanium dioxide | — | 1.0 | — | 1.0 | — | 0.30 |
| TSPP | 0.10 | 1.0 | 1.0 | 1.0 | — | 0.60 |
| Sodium saccharin | 1.40 | 0.45 | 1.40 | 0.45 | 0.30 | 0.30 |
| Sodium bicarbonate | — | — | — | — | — | 11.75 |
| Zeodent 165 | — | 1.00 | — | 1.25 | 6.00 | 2.0 |
| Zeodent 115 | — | — | — | — | 2.50 | 13.0 |
| Sylodent 783 | — | 11.0 | — | 11.0 | 19.0 | — |
| Sylodent XWA 300 | — | 10.0 | — | 10.0 | 10.0 | 10.0 |
| H2O2 (30%) | 5.71 | — | 5.71 | — | — | — |
| Sodium acid pyrophosphate | — | — | — | — | 1.50 | — |
| O-phosphoric acid | — | — | — | — | 2.8 | — |
| NaOH (50%) | — | 2.0 | — | 2.0 | — | — |
| Water | QS | QS | QS | QS | QS | QS |

To evaluate the cleaning/whitening efficacy of the three compositions, mounted bovine enamel specimens were pumiced to remove all surface stain. The teeth were then brushed for 300 strokes using a dentifrice/water slurry containing the two components of the dentifrice being studied. This procedure was repeated 9 times followed by immediately soaking each specimen covered overnight in the same dentifrice water mixture to determine the bleaching of intrinsic, below the surface stain. Before immersion, the color of the teeth was measured with a Minolta Chromameter in which L* is a measure of response to the eye to lightness and darkness, and b* is a measure of yellowness a* is a measure of blueness. The higher the L* value and lower b* value, the whiter teeth appear.

The whitening index was calculated using the following equation:

$$\Delta E = [(\Delta L^*)^2 + (\Delta a^*)^2 + (\Delta b^*)^2]^{1/2}$$

The higher the $\Delta E$ the greater the whitening effect observed. The results from this study are shown in Table II and depicted as an average increase in whiteness as seen by determining the changes in L value and $\Delta E$.

TABLE II

| Composition | $\Delta E$ | L initial | L end | $\Delta L$ |
|---|---|---|---|---|
| X | 2.55 | 46.0 | 48.4 | 2.18 |
| Y | 1.40 | 47.3 | 48.00 | 0.75 |
| Z | 0.81 | 39.7 | 39.89 | 0.20 |

The results recorded in Table II indicate that the whitening efficacy of the composition of the present invention, Composition X, provided substantially higher whitening efficacy as compared to comparative Composition Y which contained unmodified Laponite D and the prior art peroxide accelerator Mn gluconate and comparative Composition Z which contained only unmodified Laponite D.

What is claimed is:

1. A method of whitening stained or discolored teeth in the oral cavity which comprises applying to the teeth a two component dentifrice composition, the composition being comprised of a first component containing in a vehicle, a peroxide compound and a second component containing in a vehicle a Fe ion implanted synthetic silicate clay compound, the Fe implanted clay being present in an amount effective to activate the peroxide compound, the first and second components being maintained separate from each other until dispensed for application to the teeth, dispensing and mixing the separately maintained components so that the Fe ion implanted clay of the second component interacts with the peroxide compound of the first component whereby the breakdown of the peroxide compound and the release of active oxygen is accelerated and then allowing the mixed components to remain on the teeth for a time sufficient to effect accelerated whitening thereof.

2. The method of claim 1 wherein the peroxide compound is hydrogen peroxide.

3. The method of claim 1 wherein the peroxide compound is present in the first component at a concentration of about 0.1 to abut 3.0% by weight.

4. The method of claim 1 wherein the Fe ion implanted clay is a synthetic magnesium alkali metal silicate clay.

5. The method of claim 1 wherein the Fe ion implanted clay is present in the second component at a concentration of about 0.05 to about 7% by weight.

6. The method of claim 5 wherein the Fe ion implanted clay is implanted with about 0.01 to about 10% by weight of Fe ion.

7. A two component whitening dentifrice composition which exhibits rapid whitening of stained or discolored teeth, which composition comprises a first dentifrice component containing a peroxide compound and the second component containing an Fe ion implanted synthetic silicate clay, the first and second dentifrice components being maintained separate from each other until dispensed for application to teeth requiring the removal of stain and discoloration.

8. The composition of claim 7 wherein the peroxide compound is hydrogen peroxide.

9. The composition of claim 7 wherein the peroxide compound is present in the first component at a concentration of about 0.1 to about 3.0% by weight.

10. The composition of claim 7 wherein the Fe ion implanted clay is a synthetic magnesium alkali metal silicate clay.

11. The composition of claim 7 wherein the Fe ion implanted clay is present in the second component at a concentration of about 0.05 to about 7% by weight.

12. The composition of claim 11 wherein the Fe ion implanted clay is implanted with about 0.01 to about 10% by weight of Fe ion.

* * * * *